Figure 1:
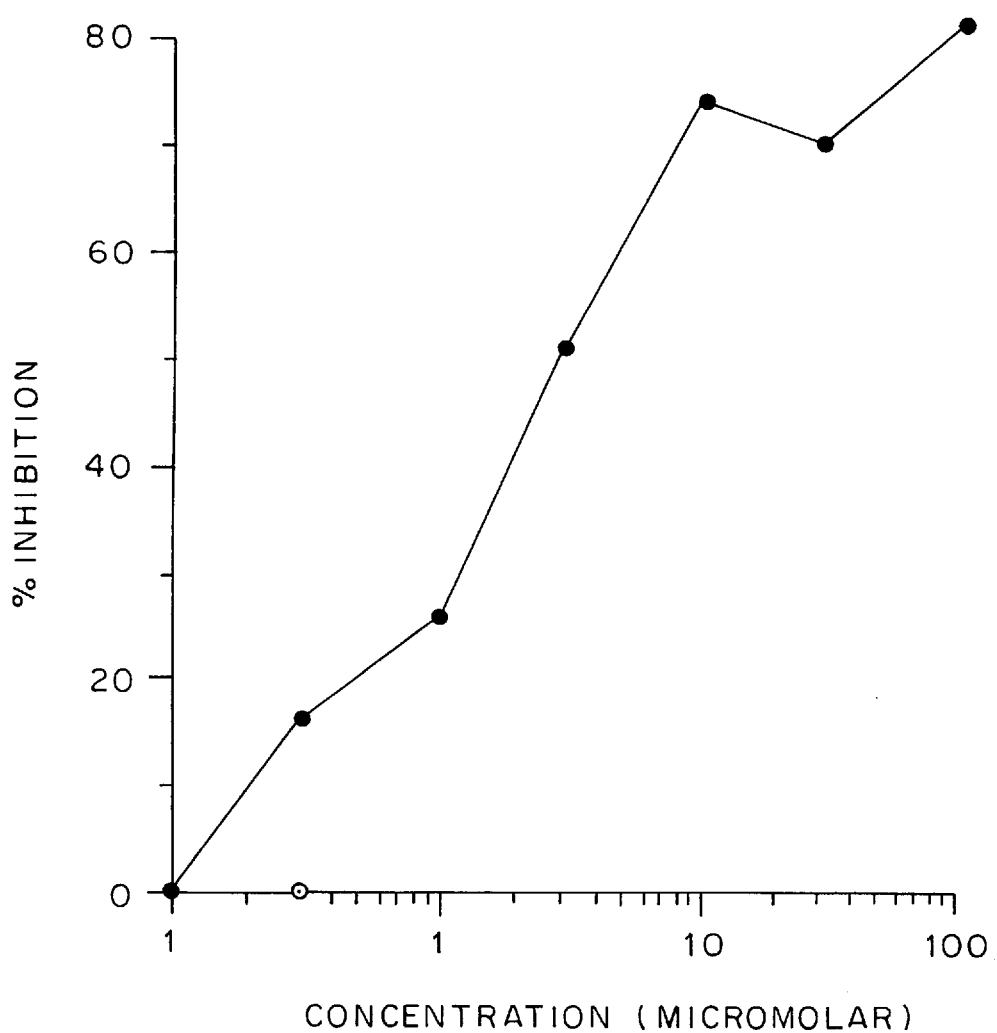

United States Patent [19]
Bergman

[11] Patent Number: 5,866,575
[45] Date of Patent: Feb. 2, 1999

[54] METHOD OF INHIBITING HIV INTEGRASE

[75] Inventor: Jan O. Bergman, Spanga, Sweden

[73] Assignee: Leif J. I. Lundblad, Stockholm, Sweden

[21] Appl. No.: 765,263

[22] PCT Filed: Jun. 19, 1995

[86] PCT No.: PCT/SE95/00747

§ 371 Date: Dec. 20, 1996

§ 102(e) Date: Dec. 20, 1996

[87] PCT Pub. No.: WO96/00067

PCT Pub. Date: Jan. 4, 1996

[30] Foreign Application Priority Data

Jun. 23, 1994 [DE] Germany .............................. 9402241-5

[51] Int. Cl.$^6$ ....................... C07D 487/04; A61K 31/495
[52] U.S. Cl. ........................................... 514/250; 544/343
[58] Field of Search .............................. 544/343; 514/250

[56] References Cited

U.S. PATENT DOCUMENTS 4,990,510  2/1991  Bergman et al. ...................... 514/250

FOREIGN PATENT DOCUMENTS

| 0 238 459 | 9/1987 | European Pat. Off. | ...... C07D 487/04 |
| 8704436 | 7/1987 | WIPO | .......................... C07D 487/04 |
| 9600067 | 1/1996 | WIPO | .......................... A61K 31/495 |
| 9619996 | 7/1996 | WIPO | .......................... A61K 31/495 |

OTHER PUBLICATIONS

Patel et al., Eur. J. Biochem., 197, 597–604, (1991).
Harmenberg et al., Antiviral Res. 15, 193–204, (1991).
Behravan et al., Biopolymers, vol. 34, 599–609, (1994).
Harmenberg et al., Antimicribial Agents and Chemotherapy, vol. 32, No. 11, p. 1720–1724 (1988).
Fesen, et al, "Inhibitors of human immunodeficiency virus intergrase"; PNAS, USA, 90:2399–2403 (1993).

Harmenberg, et al, Antiherpesvirus Activity and Mechanism of Action of Indolo–(2,3–b)Quinoxaline and Analogs; *Antimicrobial Agents and Chemotherapy*, 32(11):1720–1724.
Knotz, et al, "Experiments on the production of antiviral and antimicrobial substances"; Chemical Abstract 84:180166 and *Sci. Pharm.*, 43(4):244–260, (1975).
Vink, et al, "The human immunodeficiency virus integrase protein"; *TIG*, 9(12):433–437, (1993).
STN International, File CA, Chemical abstracts, abstract No. 64087, vol. 115, No. 7 (Aug. 19, 1991). Patel, Naina et al., "Proton NMR studies of the interaction between a self–complementary deoxyoligonucleotide duplex and indola 2,3–b–quinoaxaline derivatives active against herpes virus."
STN International, File CA, Chemical abstracts, abstract No. 64118, vol. 115, No. 7 (Aug. 19, 1991). Patel, Naina et al., "Interaction of the deoxyoligonucleotide duplex d(CGC-GATCGG)2 and anti–herpes virus active indola 2,3–b–quinoxaline derivatives."
STN International, File CA, Chemical abstracts, abstract No. 64175, vol. 115, No. 7 (Aug. 19, 1991). Harmenberg, Johan et al., "The mechanism of action of the anti–herpes virus compound 2,3–dimethyl–6 (2–dimethylaminoethyl)–6H–indolo (2,3–biquinoxaline."

*Primary Examiner*—S. Mark Clardy
*Assistant Examiner*—Sabiha N. Qazi
*Attorney, Agent, or Firm*—Browdy and Neimark

[57] ABSTRACT

Methods for inhibiting Human Immunodeficiency Virus integrase (HIV integrase) with Indoloquinoxaline derivatives of formula I are described. The definition of R1, R3 and X are as defined in specification.

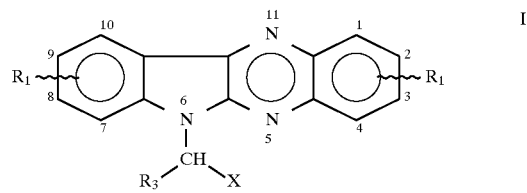

4 Claims, 1 Drawing Sheet

INHIBITION OF INTEGRATION BY COMPOUND II

METHOD OF INHIBITING HIV INTEGRASE

This application has been filed under 35 USC 371 as a national stage application of PCT/SE95/00747 filed Jun. 19, 1995.

The present invention relates to use of indolo-2,3b-quinoxalines of the general formula I

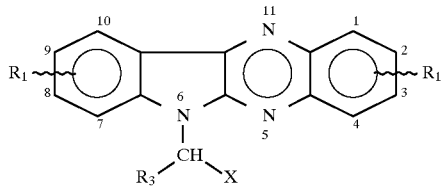

wherein $R_1$ represents hydrogen or one or several, preferably 1 to 4, similar or different substituents in the positions 1–4 and/or 7–10, selected from halogen, preferably Br, lower alkyl/alkoxy group having not more than 4carbon atoms, trifluoromethyl group, trichloromethyl group; X is a group —$(CH_2)n$—$R_2$ wherein $R_2$ represents a nitrogen containing basic residue such as $NH_2$, $NHR_4$ or $NR_5R_6$ wherein $R_4$, $R_5$ and $R_6$ independently are lower alkyl or cycloalkyl and n is an integer of from 1 to 4 and $R_3$ represents hydrogen, lower alkyl/cycloalkyl group having not more than 4 carbon atoms, and the physiologically acceptable addition products of the compounds with acids and halogen adducts, preferably adducts with iodine, iodine monochloride or iodine monobromide, as inhibitors of human immunodeficiency virus (HIV) integrase.

Substituted indoloquinoxalines of formula I have previously been demonstrated to possess valuable activity against several types of vira and several of the compounds also have been demonstrated to show a high anti-cancer effect, cf. our previous patents EP 0,238,459 and U.S. Pat. No. 4,990,510. However, they have also been shown to be inactive as enzyme inhibitors, cf. Harmenberg et al, Antimicrobial Agents and Chemotherapy, November 1988, pp. 1720–724. These studies included several virus polymerases.

Of the RNA viruses the retroviruses are of particular importance. Retroviruses are a sub-group of RNA viruses which in order to replicate must first "reverse transcribe" the RNA of their genome into DNA ("transcription" is a conventional description of the synthesis of RNA from DNA). Once in the form of DNA the viral genome may be incorporated into the host cell genome which allows it to take advantage of the transcription/translation of the host cell for the purposes of replication. Once incorporated in the host cell the viral DNA is virtually indistinguishable from the host's DNA and, in this state, the virus may persist for the life of the cell.

Human Immunodeficiency Virus (HIV) is a species of retrovirus which has been reproducibly isolated from humans with Acquired Immune Deficiency Syndrome (AIDS) or with the symptoms that frequently precede AIDS. AIDS is an immunosuppressive or immunodestructive disease that predisposes subjects to fatal opportunistic infections. AIDS is characteristically associated with a progressive depletion of T-cells, especially the helper-inducer subset bearing the $OKT^4$ surface marker. HIV is cytopathic and seems to preferentially infect and destroy T-cells bearing the $OKT^4$ marker and it is generally recognised that HIV is the etiological agent of AIDS.

The treatment of human immunodeficiency virus (HIV) is thus an increasing and important problem which needs to be solved.

It has according to the present invention unexpectedly been found that compounds of the general formula I are active against the enzyme human immunodeficiency virus integrase which was a surprising discovery in view of the fact that compounds of the same type previously had been shown to be inactive as enzyme inhibitors, cf. the article of Harmenberg et al cited above.

According to the present invention it has surprisingly been found that these indoloquinoxalines are active against the enzyme human immunodeficiency virus integrase (HIV integrase). This is evidenced from an in vitro assay in accordance with the method described by M. R. Fesen et al in Proc. Natl. Acad. Sci., USA, March 1993, Vol. 90, pp. 2399–2403.

In this test the sequental cleavage and integration reactions in the retroviral integrase assay can be illustrated by means of the following figure:

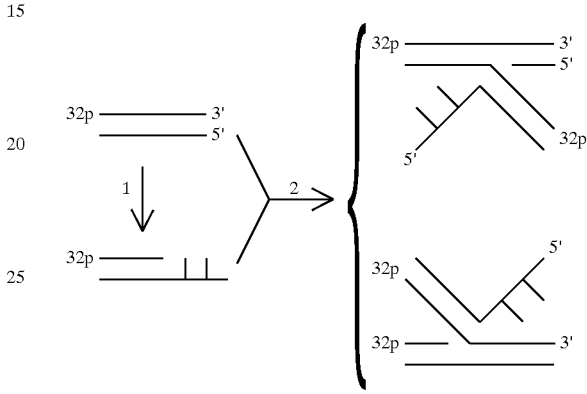

The cleavage reaction removes a dinucleotide from the 3' end of one of the strands at the integration site, thereby converting the $^{32}$P-labeled 21-mer to a 19-mer (step 1). Step 2, the integration can occur at several sites in either recipient strand. Reaction products were separated by electrophoresis and analyzed by autoradiography.

The substances of formula I used according to the present invention generally show low toxicity; thus, e.g. the compound 2,3-dimethyl-6-(N,N-dimethylaminoethyl)-6H-indoloquinoxaline having the formula II

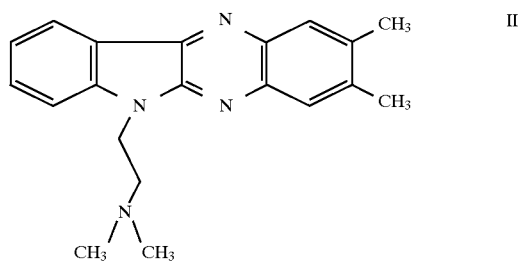

showed the following data when tested as to toxicity:
Acute toxicity
    LD p.o. rats >800 mg/kg
    LD i.v. rats >100 mg/kg
General toxicity after repeated administration
    NOEL (no observable effect level)
    i.v. rats 12.5 mg/kg for 28 days
    dermal rabbits 200 mg/kg for 28 days (except for local toxicity)

The substances of formula I used according to the present invention are prepared in accordance with the methods described in our above cited previous patents EP 0,238,459 and U.S. Pat. No. 4,990,510.

One compound of the general formula I, viz. the above-mentioned compound II, was tested as an inhibitor of human immunodeficiency virus integrase by the method described by M. R. Fesen et al in the above cited article in Proc. Natl. Acad. Sci.

The test results have been plotted in FIG. 1 wherein % inhibition is shown as a function of concentration.

Compounds of the general structure I form salts with reverse transcriptase inhibiting phosphonoalkanoic acids (e.g. phosphonoformic acid) hence these are interesting possibilities for synergistic effects.

What is claimed is:

1. A method for inhibiting the enzyme human immunodeficiency virus integrase (HIV integrase), comprising contacting said enzyme with a compound having the formula I:

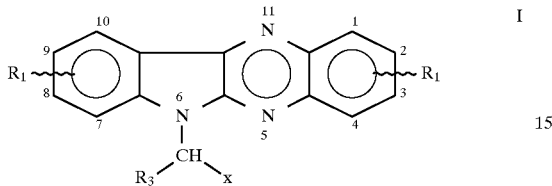

wherein $R_1$ is hydrogen or one or several similar or different substituents in the positions 1–4 and/or 7–10 selected from the group consisting of halogen, lower alkyl/alkoxy group having not more than 4 carbon atoms, trifluoromethyl group and trichloromethyl group;

X is a group $-(CH_2)_n-R_2$ wherein $R_2$ represents a nitrogen containing basic residue of $NH_2$, $NHR_4$ or $NR_5 R_6$, wherein $R_4$, $R_5$ and $R_6$ independently are lower alkyl or cycloalkyl and n is an integer of from 1 to 4; and $R_3$ is hydrogen or a lower alkyl/cycloalkyl group having not more than four carbon atoms; or a physiologically acceptable addition product thereof with an acid or halogen adduct.

2. A method in accordance with claim 1 wherein said compound has the formula

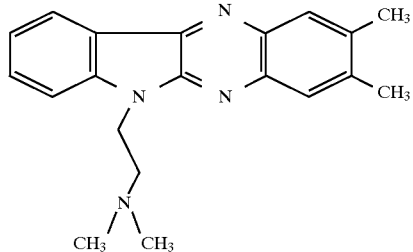

wherein $R_1$ is hydrogen or Br.

3. A method in accordance with claim 1, wherein $R_1$ represents 1 to 4 similar or different substituents in the positions 1–4 and/or 7–10.

4. A method in accordance with claim 1, wherein said compound is a physiologically acceptable addition product with an iodine adduct.

* * * * *

UNITED STATES PATENT AND TRADEMARK OFFICE
CERTIFICATE OF CORRECTION

PATENT NO.    : 5,866,575
DATED         : February 2, 1999
INVENTOR(S)   : Jan O. Bergman Page 1 of 1

It is certified that error appears in the above-identified patent and that said Letters Patent is hereby corrected as shown below:

Column 4,
Lines 8-19, delete:

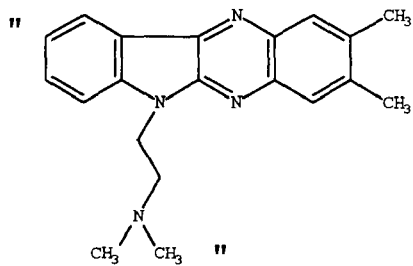

and insert therefor

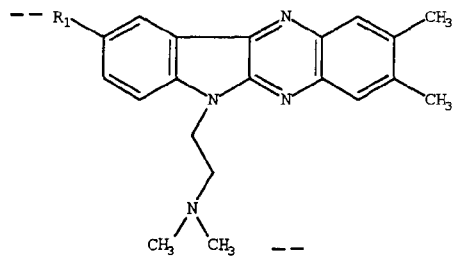

Signed and Sealed this

Twenty-ninth Day of April, 2003

JAMES E. ROGAN
*Director of the United States Patent and Trademark Office*